US012594340B2

(12) United States Patent
Lane et al.

(10) Patent No.: US 12,594,340 B2
(45) Date of Patent: Apr. 7, 2026

(54) TREATING INFLAMMATION USING LLP2A-BISPHOSPHONATE CONJUGATES AND MESENCHYMAL STEM CELLS

(71) Applicant: The Regents of the University of California, Oakland, CA (US)

(72) Inventors: Nancy E. Lane, Hillsborough, CA (US); Ruiwu Liu, Sacramento, CA (US); Wei Yao, El Dorado Hills, CA (US); Kit S. Lam, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 425 days.

(21) Appl. No.: 17/142,026

(22) Filed: Jan. 5, 2021

(65) Prior Publication Data

US 2021/0401993 A1 Dec. 30, 2021

Related U.S. Application Data

(63) Continuation of application No. 15/025,490, filed as application No. PCT/US2014/059173 on Oct. 3, 2014, now abandoned.

(60) Provisional application No. 61/887,275, filed on Oct. 4, 2013.

(51) Int. Cl.

| | |
|---|---|
| ***A61K 47/54*** | (2017.01) |
| ***A61K 9/00*** | (2006.01) |
| ***A61K 9/08*** | (2006.01) |
| ***A61K 31/663*** | (2006.01) |
| ***A61K 35/28*** | (2015.01) |
| ***A61K 47/64*** | (2017.01) |

(52) U.S. Cl.

CPC .......... *A61K 47/548* (2017.08); *A61K 9/0019* (2013.01); *A61K 9/08* (2013.01); *A61K 31/663* (2013.01); *A61K 35/28* (2013.01); *A61K 47/64* (2017.08)

(58) Field of Classification Search

None

See application file for complete search history.

(56) References Cited

U.S. PATENT DOCUMENTS

| | | | | |
|---|---|---|---|---|
| 9,119,884 | B2 | 9/2015 | Lam et al. | |
| 9,561,256 | B2 | 2/2017 | Lam et al. | |
| 10,494,401 | B2 * | 12/2019 | Lam | A61P 19/08 |
| 2013/0244963 | A1 | 9/2013 | Sinha et al. | |
| 2016/0243250 | A1 | 8/2016 | Lane et al. | |
| 2017/0174722 | A1 | 6/2017 | Lam et al. | |
| 2019/0076448 | A1 | 3/2019 | Lane et al. | |
| 2021/0205338 | A1 * | 7/2021 | Lane | A61K 47/64 |

FOREIGN PATENT DOCUMENTS

| | | |
|---|---|---|
| WO | 2012/031228 A2 | 3/2012 |
| WO | 2013/032527 A1 | 3/2013 |

OTHER PUBLICATIONS

Johns Hopkins Medicine, "Anatomy of the Bone," available online at www.hopkinsmedicine.org/health/wellness-and-prevention/anatomy-of-the-bone, 2 pages (accessed on Oct. 23, 2023) (Year: 2023).*
Cambridge Dictionary, available online at https://dictionary.cambridge.org/us/dictionary/english/prevention, 10 pages (accessed on Oct. 23, 2023) (Year: 2023).*
Gupta et al., Stem Cell Res. 3:25 (2012) (Year: 2012).*
Bullough et al., Annals Rheumatic Dis. 49:412-420 (1990) (Year: 1990).*
Fernandez-Martin et al., Arthritis Res. Ther. 23:14 pages (2021) (Year: 2021).*
Lopez-Santalla et al., EBioMedicine 69:9 pages (2021) (Year: 2021).*
Furman et al., Nat. Med. 25:1822-1832 (2019) (Year: 2019).*
Nih, "Inflammation," Natl. Inst. Environ. Health Sci., available online at www.niehs.nih.gov/health/topics/conditions/inflammation, 6 pages (first available 2021) (Year: 2021).*
Drake, V., "Inflammation," Linus Pauling Institute, Oregon State University, available online at https://lpi.oregonstate.edu/mic/health-disease/inflammation, 20 pages (first available 2010) (Year: 2010).*
Cleveland Clinic, "Synovitis", Cleveland Clinic, available online at https://my.clevelandclinic.org/health/diseases/synovitis, 13 pages (2023) (Year: 2023).*
Bottcher et al., Arthritis Res. Ther. 10:103 (2008) (Year: 2008).*
Rehman et al., Arthritis Res 3:221-227 (2001) (Year: 2001).*
Goldring et al., Arthritis Res. 2:33-37 (2000) (Year: 2000).*
Vieira-Sousa et al., The Open Rheumatol. J. (Suppl. 1:M4): 115-122 (2011) (Year: 2011).*
Lubberts et al., Madame Curie Bioscience Database, available online at https://www.ncbi.nlm.nih.gov/books/NBK6288/, 12 pages (first available 2000) (Year: 2000).*
"Inflammatory Arthritis", Arthritis Foundation, available online at http://www.arthritis.org/about-arthritis/types/inflammatoryarthritis/, accessed Jan. 17, 2018, 2 pages.
"The Mouse", Available online at URL: http://web.jhu.edu/animalcare/procedures/mouse.html, accessed Apr. 12, 2019, 8 pages.

(Continued)

*Primary Examiner* — Thea D'Ambrosio

(74) *Attorney, Agent, or Firm* — Kilpatrick Townsend & Stockton LLP

(57) ABSTRACT

The present invention provides methods of treating a subject having a primary inflammatory disease or disorder comprising administering to the subject a composition comprising a conjugate of an LLP2A peptidomimetic ligand and a bisphosphonate drug, wherein the composition comprising the LLP2A-bisphosphonate conjugate enhances the delivery of mesenchymal stem cells to a site of inflammation. Methods of enhancing an anti-inflammatory or immunomodulatory property of mesenchymal stem cells, comprising administering to a subject in need thereof the mesenchymal stem cells and a composition comprising a conjugate of an LLP2A peptidomimetic ligand and a bisphosphonate drug, are also provided.

9 Claims, 6 Drawing Sheets

(56) References Cited

OTHER PUBLICATIONS

Extended European Search Report for EP Application No. EP14850853.4, mailed On May 15, 2017, 7 pages.
International Search Report and Written Opinion, for International Patent Application No. PCT/US2014/059173, mailed Dec. 22, 2014, 11 pages.
Bernstein, "The Link Between RA and Bone Loss", Arthritis Foundation, Available online at https://www.arthritis.org/about-arthritis/types/osteoporosis/articles/bone-density.php, Dec. 6, 2019, 2 pages.
Gonzalez et al., "Treatment of Experimental Arthritis by Inducing Immune Tolerance with Human Adipose-Derived Mesenchymal Stem Cells.", Arthritis & Rheumatism, vol. 60, 2009, pp. 1006-1019.
Guan et al., "Directing mesenchymal stem cells to bone to augment bone formation and increase bone mass", Nature Medicine, vol. 18, Issue 3, Mar. 2012, pp. 456-463.
Kang, L. et al., "The Immunomodulation Effect of UC-MSC on the Inflammatory Chemokines of Rats with Collagen Type II Induced Arthritis", Chinese Journal of Thrombosis and Hemostasis, vol. 18, Issue No. 6, 2012, pp. 247-250.
Lane N. E. et al., "Glucocorticoid-treated mice have localized changes in trabecular bone material properties and osteocyte lacunar size that are not observed in placebo-treated or estrogen-deficient mice", J. Bone Mineral Res., Mar. 2006, 21(3):466-76.
Lane N. E. et al., "Glucocorticoid-induced bone fragility: New Insights", Annals of the New York Academy of Sciences, Mar. 2010, 1192(1):81-3.
Liu et al., "Therapeutic Potential of Human Umbilical Cord Mesenchymal Stem Cells in the Treatment of Rheumatoid Arthritis", Arthritis Research & Therapy, vol. 12, 2010, 13 pages.
McInnes, I. B. et al., "Cytokines in the Pathogenesis of Rheumatoid Arthritis", Nature Review Immunology, vol. 7, Jun. 2007, pp. 429-442.
Njeh et al., "Bone Loss Quantitative Imaging Techniques for Assessing Bone Mass in Rheumatoid Arthritis", Arthritis Res., vol. 2, No. 6, Aug. 3, 2000, pp. 446-450.
Pisetsky et al., "Advances in the Treatment of Inflammatory Arthritis", Best Pract. Res. Clin. Rheumatol, vol. 26, No. 2, Apr. 2012, pp. 251-261.
Stemmler et al., "Biomechanical properties of bone are impaired in patients with ACPA-positive rheumatoid arthritis and associated with the occurrence of fractures", Ann Rheum Dis, vol. 77, Feb. 23, 2018, pp. 973-980.
Wilke et al., "Osteoarthritis", available online at http://www.clevelandclinicmeded.com/medicalpubs/diseasemanagement/rheumatology/osteoarthritis/, Aug. 2010, accessed Jun. 29, 2017, 6 pages.
Yao et al., "Reversing Bone Loss by Directing Mesenchymal Stem Cells to Bone", Stem Cells, Jul. 2, 2013; vol. 31, pp. 2003-2014.
Yao et al., "Target Delivery of Mesenchymal Stem Cells to Bone", Bone, vol. 70, Jan. 2015, pp. 62-65.

* cited by examiner

D25
D46

D46

TREATING INFLAMMATION USING LLP2A-BISPHOSPHONATE CONJUGATES AND MESENCHYMAL STEM CELLS

CROSS-REFERENCE TO RELATED APPLICATIONS

The application is a continuation of U.S. application Ser. No. 15/025,490, filed Mar. 28, 2016, which is a national stage application under 35 U.S.C. § 371 of PCT/US2014/059173, filed Oct. 3, 2014, which claims priority to U.S. Provisional Application No. 61/887,275, filed Oct. 4, 2013, each of which is incorporated by reference herein for all purposes.

STATEMENT AS TO RIGHTS TO INVENTIONS MADE UNDER FEDERALLY SPONSORED RESEARCH AND DEVELOPMENT

This invention was made with Government support under Grant Nos. AR043052, AR057515 and AR061366, awarded by the National Institutes of Health. The Government has certain rights in this invention.

BACKGROUND OF THE INVENTION

Rheumatoid Arthritis (RA) causes joint swelling and pain and over time, functional impairment. Two million Americans suffer from RA. The systemic and local effects from RA inflammation results in significant systemic and local bone loss and cartilage destruction due to activation of cytokines, such as tumor necrosis factor alpha (TNFα), interleukins and macrophage-colony stimulating factor (M-CSF) that increase osteoclast activity (Huizinga and Pincus, *Ann. Intern. Med.*, 2010, 153: ITC1-1-ITC1-15; Scott et al., *Lancet*, 2010, 376:1094-1108), and inhibit osteogenesis. TNFα stimulates osteoclastogenesis and cartilage loss by inducing the expression of receptor-activator of NF-κB ligand (RANKL) and also sensitizes the osteoclast precursors to RANKL (McInnes and Schett, *N. Engl. J. Med.*, 2011, 365:2205-2219) and enzymes that degrade the cartilage. Additionally, TNFα affects osteoblasts through an enzyme called Smad Ubiquitin Regulatory Factor 1 (Smurf1), which in turn down regulates two other proteins, Smad1 and Runx2 that are critical for bone formation (Guo et al., *J. Biol. Chem.*, 2008, 283:23084-23092). Bone loss associated with RA is further worsened by the use of the glucocorticoids (GCs), which remain frequently used for RA treatment (Lane and Yao, *Ann. N.Y. Acad. Sci.*, 2010, 1192: 81-83; Lane et al., *J. Bone Miner. Res.*, 2006, 21:466-76). However, GC use creates rapid bone loss that results in a high incident fracture risk.

While traditional RA drugs like NSAIDs and GCs treat symptoms, and the newer class of TNFα blockers (Humira, Remicade and Enbrel) reverse the disease process, this class of drugs are based on bioengineered versions of proteins, and are very expensive to produce (Chimenti et al., *Autoimmun. Rev.*, 2011, 10:636-401 Marotte and Miossec, *Biologics*, 2008, 2: 663-9; Caramaschi et al, *Rheumatol. Ent.*, 2006, 26:209-14). Conventional drug therapies for RA including TNFα blockers mainly target inflammation and also reduce bone resorption; however, nearly 40% of the RA patients treated with biologics (TNF, IL-6 and B cell depleting therapy, and JAK inhibitors) do not have a significant reduction in pain and joint inflammation resulting in continued bone and cartilage destruction.

Mesenchymal stem cells (MSCs) within the bone marrow have a multi-lineage potential and represent a mixture of precursors for mesenchymal-derived cell types including osteoblasts, chondrocytes and adipocytes (Owen, M. et al., *Ciba Found Symp*, 1988, 136: p. 42-60; Bruder, S. P., et al., *J Cell Biochem*, 1994, 56(3): p. 283-94; Prockop, D. J., *Science*, 1997, 276(5309): p. 71-4). Bone cells at all maturation stages rely heavily on cell-matrix and cell-cell interactions (Mukherjee, S., et al., *J Clin Invest*, 2008, 118(2): p. 491-504; Grzesik, W. J. and P. G. Robey, *J Bone Miner Res*, 1994, 9(4): p. 487-96; Vukicevic, S., et al., *Cell*, 1990, 63(2): p. 437-45; Mbalaviele, G., et al., *J Bone Miner Res*, 2006, 21(12): p. 1821-7).

MSCs express integrins al, 2, 3, 4, 6, 11, CD51 (integrin αV), and CD29 (integrins (31) (Brooke, G., et al., Stem Cells Dev, 2008). Integrins $\alpha_1\beta_1$, $\alpha_2\beta_1$, $\alpha_v\beta_1$, $\alpha_v\beta_5$, $\alpha_5\beta_1$ and $\alpha_4\beta_1$ are reported to be expressed in the osteoblastic cells (Grzesik, W. J. and Robey, P. G., *J Bone Miner Res*, 1994, 9(4): p. 487-96; Gronthos, S., et al., *Bone*, 2001, 28(2): p. 174-81; Gronthos, S., et al., *J Bone Miner Res*, 1997. 12(8): p. 1189-97; Cowles, E. A., L. L. Brailey, and G. A. Gronowicz, *J Biomed Mater Res*, 2000, 52(4): p. 725-37). Overexpression of $\alpha_4$ integrin on MSCs has been reported to increase homing of the MSCs to bone (Mukherjee, S., et al., *J Clin Invest*, 2008, 118(2): p. 491-504).

Mesenchymal stem cells also express a variety of chemokine and cytokine receptors and can combat inflammation in a localized tissue. Chemokines and cytokines are released during the inflammation process and drive the inflammatory response. These same signaling molecules can promote the MSCs to home (e.g., migrate) to the inflammatory sites through the CXCR4 receptor or integrin β1 on the surface of the MSCs. Additionally, MSCs can regulate the innate immune response by signaling dendritic cells to direct an anti-inflammatory T-cell response or by suppressing natural killer cell functions. MSCs also affect the adaptive immune response by exerting an immunoregulatory effects through direct interaction with the activation of $CD4^+$T-cells. It has been shown that systemic MSC transplantation induces anti-inflammatory effects. However, MSCs tend not to be efficient at entering inflamed tissues.

The unmet medical needs for RA or inflammatory arthritis are compositions and methods for preventing and/or treating joint inflammation and immune modulation associated with inflammatory disease. Surprisingly, the present invention meets these and other needs.

BRIEF SUMMARY OF THE INVENTION

In one aspect, the present invention relates to methods for reducing one or more signs or symptoms of arthritis pain, e.g., in rheumatoid arthritis or inflammatory arthritis. In some embodiments, the method comprises administering to a subject having arthritis (e.g., rheumatoid arthritis or inflammatory arthritis) a composition comprising a conjugate of an LLP2A peptidomimetic ligand and a bisphosphonate drug. In some embodiments, the composition comprises a conjugate of LLP2A and Alendronate ("LLP2A-Ale"). In some embodiments, the method further comprises administering exogenous mesenchymal stem cells.

In another aspect, the present invention relates to methods for reducing, slowing, or inhibiting cartilage and bone destruction resulting from inflammation in arthritis (e.g., in rheumatoid arthritis or inflammatory arthritis). In some embodiments, the method comprises administering to a subject having arthritis (e.g., rheumatoid arthritis or inflammatory arthritis) a composition comprising a conjugate of an LLP2A peptidomimetic ligand and a bisphosphonate drug. In some embodiments, the composition comprises a conjugate of LLP2A and Alendronate ("LLP2A-Ale"). In some embodiments, the method further comprises administering exogenous mesenchymal stem cells.

In another aspect, provided herein is a method of treating a subject having a primary inflammatory disease or disorder selected from arthritis, inflammatory arthritis, rheumatoid arthritis, synovitis, juvenile rheumatoid arthritis, ankylosing spondylitis, psoriatic arthritis, spondylarthritis, and osteoarthritis. The method comprises administering to the subject a composition including a conjugate of an LLP2A peptidomimetic ligand and a bisphosphonate drug, wherein the composition comprising the LLP2A-bisphosphonate conjugate enhances the delivery of mesenchymal stem cells to a site of inflammation.

In some embodiments, the composition comprises a conjugate of LLP2A and Alendronate ("LLP2A-Ale"). In another embodiment, the method further includes administering exogenous mesenchymal stem cells.

In some embodiments, the composition and the mesenchymal stem cells are administered sequentially. In some embodiments, the composition and the mesenchymal stem cells are administered concurrently.

In some embodiments, one or both of the composition and the mesenchymal stem cells are administered locally at the site of inflammation. In some instances, the site of inflammation is a joint.

In some embodiments, one or both of the composition and the mesenchymal stem cells are administered by injection.

In some embodiments, one or both of the composition and the mesenchymal stem cells are administered systemically. In other embodiments, one or both of the composition and the mesenchymal stem cells are administered intravenously.

In some embodiments, the subject has rheumatoid arthritis or synovitis.

In a second aspect, provided herein is a method of reducing inflammation in a subject in need thereof, the method comprising co-administering to the subject (a) a composition comprising a conjugate of an LLP2A peptidomimetic ligand and a bisphosphonate drug, and (b) mesenchymal stem cells, wherein the composition comprising the LLP2A-bisphosphonate conjugate enhances the delivery of the mesenchymal stem cells to a site of inflammation.

In some embodiments, the composition comprises a conjugate of LLP2A and Alendronate ("LLP2A-Ale"). In another embodiment, the method further includes administering exogenous mesenchymal stem cells.

In some embodiments, the composition and the mesenchymal stem cells are administered sequentially. In some embodiments, the composition and the mesenchymal stem cells are administered concurrently.

In some embodiments, one or both of the composition and the mesenchymal stem cells are administered locally at the site of inflammation. In some instances, the site of inflammation is a joint.

In some embodiments, one or both of the composition and the mesenchymal stem cells are administered by injection.

In some embodiments, one or both of the composition and the mesenchymal stem cells are administered systemically. In other embodiments, one or both of the composition and the mesenchymal stem cells are administered intravenously.

In some embodiments, one or both of the composition and the mesenchymal stem cells are administered at a subtherapeutic dose. In some embodiments, the amount of mesenchymal stem cells that is administered is no more than 70% of the amount of mesenchymal stem cells that produces a significant therapeutic effect when administered alone.

In some embodiments, the composition and the mesenchymal stem cells are administered in a series of doses separated by intervals of days or weeks.

In one embodiment, the subject in need of treatment has an inflammatory disease or disorder.

In a third aspect, provided herein is a method of treating a subject having an inflammatory disease or disorder, the method comprising co-administering to the subject (a) a composition comprising a conjugate of an LLP2A peptidomimetic ligand and a bisphosphonate drug, and (b) mesenchymal stem cells, wherein the amount of mesenchymal stem cells that is administered is a subtherapeutic dose.

In some embodiments, the inflammatory disease or disorder is selected from arthritis, rheumatoid arthritis, synovitis, juvenile rheumatoid arthritis, ankylosing spondylitis, psoriatic arthritis, spondylarthritis, and osteoarthritis. In some instances, the inflammatory disease or disorder is rheumatoid arthritis or synovitis.

In some embodiments, the composition and the mesenchymal stem cells are administered sequentially. In some embodiments, the composition and the mesenchymal stem cells are administered concurrently.

In some embodiments, one or both of the composition and the mesenchymal stem cells are administered locally at the site of inflammation. In some instances, the site of inflammation is a joint.

In some embodiments, one or both of the composition and the mesenchymal stem cells are administered by injection.

In some embodiments, one or both of the composition and the mesenchymal stem cells are administered systemically. In other embodiments, one or both of the composition and the mesenchymal stem cells are administered intravenously.

In some embodiments, the amount of mesenchymal stem cells that is administered is no more than 70% of the amount of mesenchymal stem cells that produces a significant therapeutic effect when administered alone.

In some embodiments, the composition and the mesenchymal stem cells are administered in a series of doses separated by intervals of days or weeks.

In a fourth aspect, provided herein is a method of enhancing an anti-inflammatory or immunomodulatory property of mesenchymal stem cells, comprising administering to a subject the mesenchymal stem cells and a composition comprising a conjugate of an LLP2A peptidomimetic ligand and a bisphosphonate drug.

In some embodiments, the inflammatory disease or disorder is selected from arthritis, rheumatoid arthritis, synovitis, juvenile rheumatoid arthritis, ankylosing spondylitis, psoriatic arthritis, spondylarthritis, and osteoarthritis. In some instances, the inflammatory disease or disorder is rheumatoid arthritis or synovitis.

In some embodiments, the mesenchymal stem cells are administered in an amount that is not sufficient to significantly reduce inflammation or have a significant immunomodulatory effect in a subject administered mesenchymal stem cells in the absence of the composition comprising the LLP2A-bisphosphonate conjugate.

In some embodiments, the composition and the mesenchymal stem cells are administered sequentially. In some embodiments, the composition and the mesenchymal stem cells are administered concurrently.

In some embodiments, one or both of the composition and the mesenchymal stem cells are administered locally at the site of inflammation. In some instances, the site of inflammation is a joint.

In some embodiments, one or both of the composition and the mesenchymal stem cells are administered by injection.

In some embodiments, one or both of the composition and the mesenchymal stem cells are administered systemically. In other embodiments, one or both of the composition and the mesenchymal stem cells are administered intravenously.

In some embodiments, the composition and the mesenchymal stem cells are administered in a series of doses separated by intervals of days or weeks.

Other objects, features, and advantages of the present invention will be apparent to one of skill in the art from the following detailed description and figures.

DETAILED DESCRIPTION OF THE INVENTION

I. Introduction

Figure 1A:
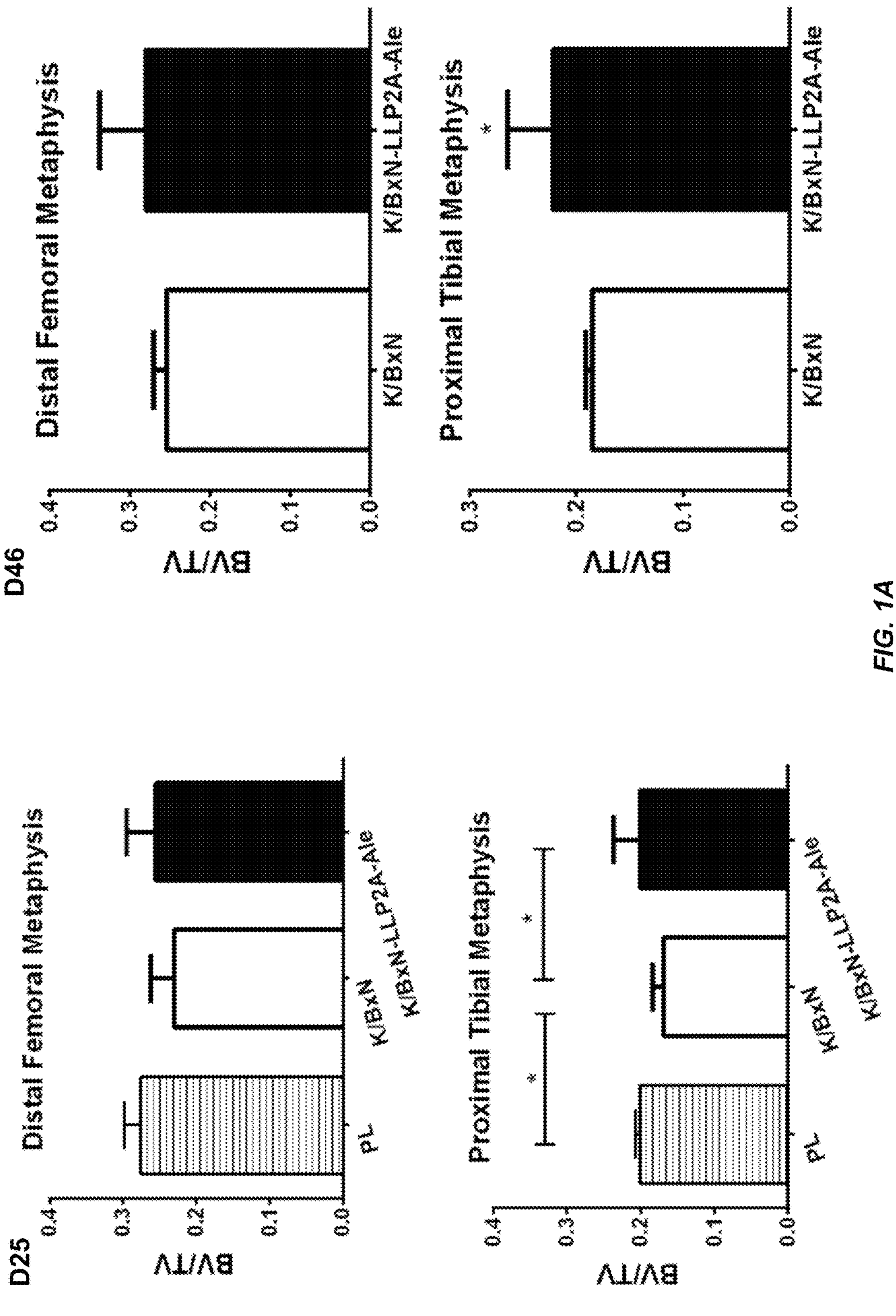
FIG. 1A-B. LLP2A-Ale prevented bone loss in periarticular regions and tibial trabeculae associated with rheumatoid arthritis. (A) Left column: Bone volume/tissue volume fraction measured at the distal femur (upper panels) or proximal tibia (lower panels) for K/B×N serum or K/B×N serum and LLP2A-Ale (100 μg/kg IV at day 4) at day 25 (left column) or day 46 (right column). (B) Representative microCT images of the distal femur-knee join-proximal tibia for K/B×N serum (left column) or K/B×N serum and LLP2A-Ale (100 μg/kg IV at day 4) (right column) at day 25 (upper panels) or day 46 (lower panels).

The present invention relates to the surprising discovery that compounds and pharmaceutical compositions of a peptidomimetic ligand, e.g., LLP2A, conjugated with a bisphosphonate, e.g., alendronate, exhibit immune-modulating effects and are useful in decreasing or preventing inflammation. Without being bound to a particular theory, it is believed that the conjugates guide stem cells (e.g., mesenchymal stem cells) to a site of inflammation, where the stem cells exert immunoregulatory or immunosuppressive effects. Thus, the conjugates described herein, when administered alone or in combination with mesenchymal stem cells, can increase the efficacy of mesenchymal stem cells in inducing inflammatory or immunomodulatory effects.

As described herein, in one aspect the peptidomimetic ligand-bisphosphonate (e.g., LLP2A-alendronate) conjugates, alone or in combination with mesenchymal stem cells, can be used for the treatment of inflammation, for example in a primary inflammatory disease or disorder such as but not limited to arthritis, inflammatory arthritis, rheumatoid arthritis, synovitis, juvenile rheumatoid arthritis, ankylosing spondylitis, psoriatic arthritis, spondylarthritis, and osteoarthritis. In another aspect, the treatment of inflammation at a bone, joint, or bone-associated tissue that is inflamed (e.g., in a joint afflicted with synovitis) can also slow or prevent destruction of that bone, joint, or tissue which is due to inflammation.

II. Definitions

The abbreviations used herein have their conventional meaning within the chemical and biological arts. As used herein, the following terms have the meanings ascribed to them unless specified otherwise.

As used herein, the terms "a" or "an," when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

As used herein, the term "Ale" or "Alen" refers to Alendronate.

As used herein, the term "peptide" refers to a compound made up of a single chain of D- or L-amino acids or a mixture of D- and L-amino acids joined by peptide bonds. Generally, peptides are about 2 to about 50 amino acids in length. Preferably, the peptides of the present invention are about 2 to about 25 amino acids in length, more preferably 3 to 20 amino acids in length, and most preferably 3 to 10 amino acids in length.

As used herein, the term "amino acid" refers to naturally occurring, unnatural, and synthetic amino acids, as well as amino acid analogs and amino acid mimetics that function in a manner similar to the naturally occurring amino acids. Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic carboxylic acids (acetic acid, propionic acid, glutamic acid, citric acid and the like), organic sulfonic acids (methanesulfonic acid), salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention include salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

As used herein, the term "hydrate" refers to a compound that is complexed to at least one water molecule. The compounds of the present invention can be complexed with from 1 to 10 water molecules.

As used herein, the terms "pharmaceutically acceptable excipient" and "pharmaceutically acceptable carrier" refer to a substance that aids the administration of an active agent to and absorption by a subject. "Pharmaceutically acceptable excipient" refers to an excipient that can be included in the compositions of the invention and that causes no significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

As used herein, the term "isomers" refers to compounds with the same chemical formula but which are structurally distinguishable.

As used herein, the term "mesenchymal stem cell" refers to a multipotent stem cell (i.e., a cell that has the capacity to differentiate into a subset of cell types) that can differentiate into a variety of cell types, including osteoblasts, chondrocytes, and adipocytes. Mesenchymal stem cells can be obtained from a variety of tissues, including but not limited to bone marrow tissue, adipose tissue, muscle tissue, birth tissue (e.g., amnion, amniotic fluid, or umbilical cord tissue), skin tissue, bone tissue, and dental tissue.

As used herein, "immunomodulation" and "immunomodulatory" mean causing, or having the capacity to cause, a detectable change in an immune response, and the ability to cause a detectable change in an immune response.

gate and/or stem cells as described herein) that is below that which is required to produce a significant desired clinical benefit for a subject (e.g., an anti-inflammatory or immunomodulatory effect) when the composition is administered alone.

As used herein, the terms "treat," "treating," and "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; and/or improving a patient's physical or mental well-being. The treatment or amelioration of symptoms can be based on objective or subjective parameters; including the results of a physical examination, neuropsychiatric exams, and/or a psychiatric evaluation.

III. Compositions for Treating Inflammation and Inflammatory Diseases

In one aspect, the present invention relates to the use of a peptidomimetic ligand, e.g., LLP2A, conjugated with a bisphosphonate, e.g., alendronate, alone or in combination with mesenchymal stem cells, for treating inflammation. In another aspect, the present invention relates to the use of a peptidomimetic ligand, e.g., LLP2A, conjugated with a bisphosphonate, e.g., alendronate, alone or in combination with mesenchymal stem cells, for enhancing an anti-inflammatory or immunomodulatory property of mesenchymal stem cells.

LLP2A-Bisphosphonate Conjugates

In some embodiments, the present invention relates to LLP2A compounds conjugated to a bisphosphonate drug:

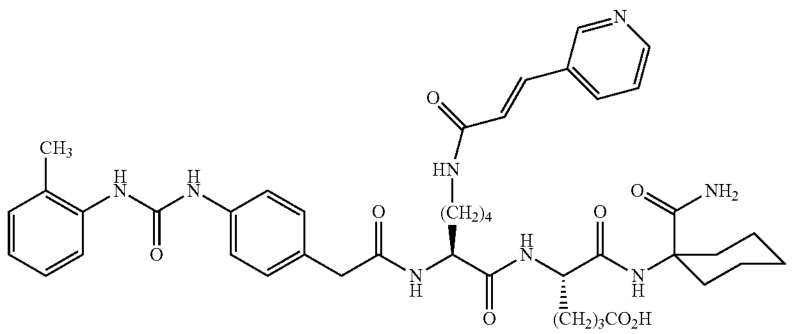

LLP2A

As used herein, the terms "patient" and "subject" interchangeably refer to a living organism having or prone to a condition that can be treated by administration of a pharmaceutical composition as provided herein. Non-limiting examples include humans, other mammals and other non-mammalian animals.

As used herein, the term "therapeutically effective amount" refers to an amount of a pharmaceutical composition (e.g., a conjugate and/or stem cells as described herein) useful for treating or ameliorating an identified disease or condition, or for exhibiting a detectable therapeutic or inhibitory effect. The effect can be detected by any assay method known in the art.

As used herein, the term "subtherapeutic dose" refers to an amount of a pharmaceutical composition (e.g., a conju- Bisphosphonates are widely used for the treatment of osteoporosis. This class of drugs is also used as a "vehicle" for delivering bone-targeted drugs to osseous tissue as prodrugs based on their biphosphonic moiety. Bisphosphonates have been used to deliver sustained release diclofenac, a non-steroidal anti-inflammatory drug to bone in rats (Hirabayashi, H., et al., *J Control Release,* 2001, 70(1-2): p. 183-91). The bisphosphonate dose needed for this drug-delivery purpose is usually 10-100 fold lower than the doses needed for the treatments of osteoporosis, hypocalcaemia, Paget's disease or metastatic bone cancer. Bisphosphonate drugs useful with the present invention include any suitable bisphosphonate compound. Exemplary bisphosphonate drugs include, but are not limited to, Etidronate (Didronel), Clodronate (Bonefos, Loron), Tiludronate (Skelid), Pamidronate (APD, Aredia), Neridronate, Olpadronate, Alendronate (Fosamax), Ibandronate (Boniva), Risedronate (Actonel) and Zoledronate (Zometa). Additional bisphosphonates are described below in greater detail. One of skill in the art will appreciate that other bisphosphonates are useful in the present invention. In some embodiments, the bisphosphonate is Alendronate.

In some embodiments, the present invention provides a compound of Formula I (e.g., LLP2A-Ale):

monium salts. Other salts with organic bases include salts with diethylamine, diethanolamine, meglumine, and N,N'-dibenzylethylenediamine.

Acid addition salts, such as mineral acids, organic carboxylic and organic sulfonic acids, e.g., hydrochloric acid, methanesulfonic acid, maleic acid, are also possible provided a basic group, such as pyridyl, constitutes part of the structure.

(I)

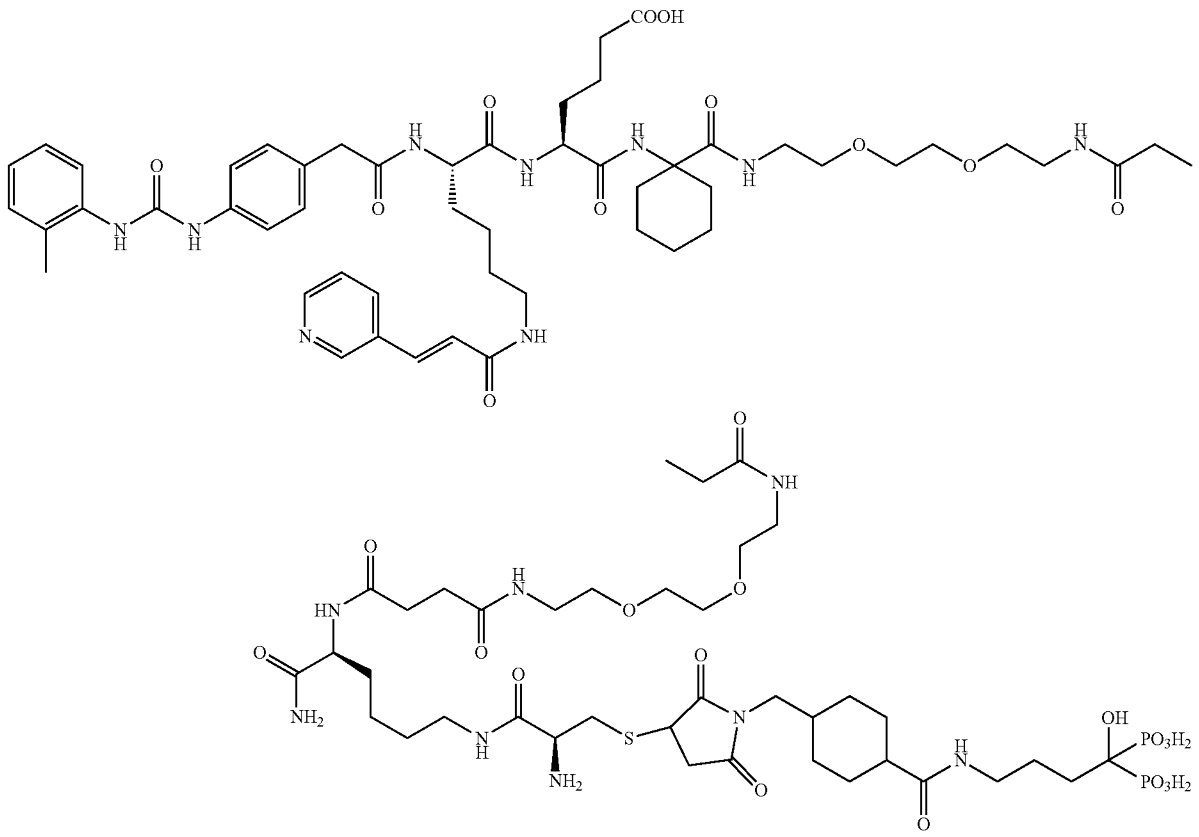

LLP2A-Ale

In some embodiments, the salts, hydrates, solvates, prodrug forms, isomers, and metabolites of LLP2A compounds conjugated to a bisphosphonate drug (e.g., a compound of Formula I) are provided.

Salts include, but are not limited, to sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases including alkali metal salts such as sodium salts, lithium salts, and potassium salts; alkaline earth metal salts such as calcium salts, and magnesium salts; aluminum salts; and ammonium salts, such as ammonium, trimethyl-ammonium, diethylammonium, and tris-(hydroxymethyl)-methyl-ammonium salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

The present invention also provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the invention can be synthesized by a variety of methods known to one of skill in the art (see *Comprehensive Organic Transformations* by Richard C. Larock, 1989) or by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. One of skill in the art will appreciate that other methods of making the compounds are useful in the present invention.

As an example, LLP2A-Alendronate (LLP2A-Ale) can be made by conjugate addition of the sulfhydryl group of LLP2A-Lys(D-Cys) to alendronate-maleimide (Ale-Mal), the latter can be prepared in situ from alendronate and sulfosuccinimidyl-4-(N-maleimidomethyl)cyclohexane-1-carboxylate (sulfo-SMCC). LLP2A-Lys(D-Cys) can be prepared by solid phase synthesis from several commercially available starting materials and one characterized intermediate, 4-[(N'-2-methylphenyl)ureido]phenylacetic acid (UPA), which can also prepared from commercially available starting materials. Methods of making LLP2A compounds conjugated to a bisphosphonate drug, including a detailed description of the synthesis of LLP2A-Ale, are found in, e.g., International Appl. Pub. Nos. WO 2012/031228 and WO 2013/032527, the disclosures of which are herein incorporated in their entirety for all purposes.

Mesenchymal Stem Cells

In some embodiments, a composition comprising a conjugate of an LLP2A peptidomimetic ligand and a bisphosphonate drug (e.g., LLP2A-Ale) is co-administered with mesenchymal stem cells (MSCs) to modulate an immune response, or to modulate the activity of a plurality of one or more types of immune cells, in vivo. Without being bound to a particular theory, it is believed that the conjugates guide the mesenchymal stem cells to a site of inflammation, where the mesenchymal stem cells exert immunoregulatory or immunosuppressive effects. In some embodiments, endogenous mesenchymal stem cells in the subject are recruited by the conjugate to a site of inflammation.

The mesenchymal stem cells that are administered may be a homogeneous composition or may be a mixed cell population comprising MSCs or enriched for MSCs. Suitable MSCs may be obtained or derived, e.g., from bone marrow mononuclear cells collected from aspirates of bone marrow. In some embodiments, homogeneous mesenchymal stem cell compositions are obtained by culturing adherent marrow or periosteal cells in an appropriate culture medium, and the mesenchymal stem cell compositions may be obtained by culturing adherent marrow or periosteal cells to obtain an expanded MSC population. The MSCs may be identified by specific cell surface markers which are identified with unique monoclonal antibodies. A method for obtaining a cell population enriched in mesenchymal stem cells is described, for example, in U.S. Pat. No. 5,486,359, incorporated by reference herein. Sources for mesenchymal stem cells include, but are not limited to, bone marrow, muscle, adipose, placental tissue, umbilical cord tissue, tooth pulp, skin tissue, peripheral blood, and synovial membranes. Mesenchymal stem cells (MSCs) may be purified using methods known in the art (see, e.g., Wakitani et al., 1995; Fukuda and Yuasa, 2006; Woodbury et al., 2000; Deng et al., 2001; Kim et al., 2006; Mareschi et al., 2006; Krampera et al., 2007).

Compositions that are enriched for MSCs (e.g., having greater than about 95%, usually greater than about 98%, of mesenchymal stem cells) can be achieved using techniques for isolation, purification, and culture expansion of mesenchymal stem cells that are known in the art. As a non-limiting example, isolated, cultured mesenchymal stem cells may comprise a single phenotypic population (e.g., at least about 95% or about 98% homogeneous) by flow cytometric analysis of expressed surface antigens. The desired cells in such composition are identified as expressing one or more cell surface markers for the cell type (e.g., CD73 or CD105).

The mesenchymal stem cells may be administered by a variety of procedures. In some embodiments, the mesenchymal stem cells are administered systemically, such as by intravenous, intraarterial, or intraperitoneal administration.

The mesenchymal stem cells may be from a spectrum of sources including autologous, allogeneic, or xenogeneic.

In an embodiment, the mesenchymal stem cells are administered in an amount of from about $1\times10^4$ cells/kg to about $1\times10^8$ cells/kg of body weight (e.g., about $1\times10^4$ cells/kg, about $1\times10^5$ cells/kg, about $1\times10^6$ cells/kg, about $1\times10^7$ cells/kg, or about $1\times10^8$ cells/kg). The amount of mesenchymal stem cells to be administered is dependent upon a variety of factors, including the age, weight, and sex of the patient, the autoimmune disease to be treated, and the extent and severity thereof.

The mesenchymal stem cells may be administered in conjunction with an acceptable pharmaceutical carrier. For example, the mesenchymal stem cells may be administered as a cell suspension in a pharmaceutically acceptable liquid medium or gel for injection or topical application. In one embodiment, the pharmaceutically acceptable liquid medium is a saline solution. The saline solution may contain additional materials such as dimethylsufoxide (DMSO) and human serum albumin.

IV. Formulation and Administration

The compositions of the present invention (e.g., LLP2A-alendronate conjugates and/or mesenchymal stem cells) can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. Pharmaceutical compositions can be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal, or intraurethral injection or infusion. In some embodiments, administration is by injection, that is, intravenously, intramuscularly, intracutaneously, subcutaneously, intraduodenally, or intraperitoneally. Accordingly, the present invention also provides pharmaceutical compositions including a pharmaceutically acceptable carrier or excipient and either a compound of the present invention, or a pharmaceutically acceptable salt of a compound of the present invention.

The formulations of the invention are also suitable for administration in all body spaces/cavities, including but not limited to pleura, peritoneum, cranium, mediastinum, pericardium, bursae or bursal, epidural, intrathecal, intraocular, intra-articular, intra-discal, intra-medullary, perispinal, etc.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton PA.

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound.

In general, the type of carrier is selected based on the mode of administration. A pharmaceutical composition (e.g., for oral administration or delivery by injection) can be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The compositions typically include a conventional pharmaceutical carrier or excipient and may additionally include other medicinal agents, carriers, adjuvants, diluents, tissue permeation enhancers, solubilizers, and the like. In some embodiments, the composition will contain about 0.01% to about 90%, e.g., about 0.1% to about 75%, about 0.1% to 50%, or about 0.1% to 10% by weight of a conjugate and/or mesenchymal stem cells, with the remainder consisting of suitable pharmaceutical carrier and/or excipients. Appropriate excipients can be tailored to the particular composition and route of administration by methods well known in the art, e.g., Remington's Pharmaceutical Sciences, supra.

Suitable solid excipients include, but are not limited to, magnesium carbonate; magnesium stearate; calcium phosphate; calcium silicate; talc; pectin; dextran, dextrin, and cyclodextrin inclusion complexes; a low melting wax; cocoa butter; carbohydrates; sugars including, but not limited to, lactose, dextrose, sucrose, mannitol, or sorbitol; starches including, but not limited to, starch from corn, wheat, rice, potato, or other plants; cellulose such as methyl cellulose, hydroxypropylmethyl-cellulose, or sodium carboxymethylcellulose; and gums including arabic, tragacanth, and acacia; as well as proteins including, but not limited to, gelatin, collagen; microcrystalline cellulose, water, saline, syrup, ethylcellulose, and polyacrylic acids such as Carbopols, e.g., Carbopol 941, Carbopol 980, Carbopol 981, etc.; lubricating agents; mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents; biodegradable polymer beads. If desired, disintegrating or solubilizing agents may be added, such as the cross-linked polyvinyl pyrrolidone, agar, alginic acid, alginates, or a salt thereof, such as sodium alginate.

A pharmaceutically acceptable carrier may include physiologically acceptable compounds that act, for example, to stabilize the compounds of the present invention or modulate their absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the compounds of the present invention and on the particular physio-chemical characteristics of the compounds of the present invention.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain compounds of the present invention mixed with fillers or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

Liquid form preparations include solutions, suspensions, and emulsions, for example, water or water/propylene glycol solutions. Liquid compositions can be prepared, e.g., by dissolving or dispersing a conjugate and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a compound of the present invention in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For oral administration, the compositions can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the conjugate and/or mesenchymal stem cells, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The conjugate and/or mesenchymal stem cells can also be formulated into a suppository disposed, for example, in a polyethylene glycol (PEG) carrier.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

In some embodiments, the pharmaceutical composition is a slow release formulation. Slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone, methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

The pharmaceutical preparation is preferably in unit dosage form. The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of LLP2A-bisphosphonate conjugates and/or mesenchymal stem cells. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Methods for preparing such dosage forms are known to those skilled in the art (see, for example, Remington's Pharmaceutical Sciences, supra. The composition to be administered contains a quantity of the LLP2A-bisphosphonate conjugates and/or mesenchymal stem cells in a pharmaceutically effective amount for relief of a condition being treated when administered in accordance with the teachings of this invention. In addition, pharmaceutically acceptable salts of the conjugates of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, $4^{th}$ Ed. (New York: Wiley-Interscience, 1992).

Generally, administered dosages will be effective to deliver picomolar to micromolar concentrations of the LLP2A-bisphosphonate conjugates and/or mesenchymal stem cells to the appropriate site or sites. However, one of ordinary skill in the art understands that the dose administered will vary depending on a number of factors, including, but not limited to, the particular conjugate to be administered, the mode of administration, the type of application (e.g., imaging, therapeutic), the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage.

In some embodiments, the dosage of one or both of the conjugate (e.g., LLP2A-Ale) and the mesenchymal stem cells is a subtherapeutic dose. In some embodiments, the subtherapeutic dose of the conjugate (e.g., LLP2A-Ale) and/or the mesenchymal stem cells is no more than 70%, no more than 60%, no more than 50%, no more than 40%, no more than 30%, or no more than 20% of the amount of conjugate and/or mesenchymal stem cells that produces a significant therapeutic effect when administered alone.

In some embodiments, the dosage of the mesenchymal stem cells is an amount that is not sufficient to significantly reduce inflammation, or is an amount that does not have a significant immunomodulatory effect, in a subject when administered in the absence of the LLP2A-bisphosphonate conjugate. In some embodiments, the dosage of mesenchymal stem cells that is not sufficient to significantly reduce inflammation or that does not have a significant immunomodulatory effect is determined by administering varying dosages of mesenchymal stem cells to subjects in the absence of administering an LLP2A-bisphosphonate conjugate and measuring the therapeutic effect, if any, of the administration of mesenchymal stem cells on inflammation or immunomodulation. In some embodiments, an immunomodulatory effect or a reduction of inflammation is not "significant" if the change in immunomodulatory effect or reduction of inflammation is less than 10% or less than 5% compared to a baseline or control (e.g., compared to the level of immunomodulatory effect or inflammation in a subject prior to administering the mesenchymal stem cells). Reduction of inflammation can be determined, for example, by measuring the level of one or more markers of inflammation, such as but not limited to C-reactive protein, tumor necrosis factor alpha (TNF-$\alpha$), nuclear factor kappa-B (NF-$\kappa$B), an interleukin (e.g., IL6 and soluble IL-2R), antibodies against citrulline modified proteins (anti-CCP), or rheumatoid factor. Reduction of inflammation can also be determined, for example, by measuring erythrocyte sedimentation rate (ESR) in a blood sample from the subject.

In some embodiments, co-administration of the LLP2A-bisphosphonate conjugates and the mesenchymal stem cells enhances the therapeutic effects such that administration of one or both of the LLP2A-bisphosphonate conjugate and the mesenchymal stem cells can be administered at a reduced amount or at a reduced frequency relative to the amount and/or frequency that would be required to induce a therapeutic effect if the LLP2A-bisphosphonate conjugate or the mesenchymal stem cells were administered alone. For example, in some embodiments, one or both of the LLP2A-bisphosphonate conjugate and the mesenchymal stem cells can be administered 10%, 20%, 30%, 40%, 50%, 60%, or 70% less often than if administered alone. In some embodiments, one or both of the LLP2A-bisphosphonate conjugates and the mesenchymal stem cells can be administered in an amount that is about 10%, 20%, 30%, 40%, 50%, 60%, or 70% less than the amount that would be required to induce a therapeutic effect if the LLP2A-bisphosphonate conjugate or the mesenchymal stem cells were administered alone.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

In some embodiments, the compositions described herein (e.g., LLP2A-Ale conjugates and the mesenchymal stem cells) are administered in combination with one another for treating an inflammatory disease or disorder, reducing signs or symptoms of inflammation, or promoting or enhancing an anti-inflammatory or immunomodulatory property of mesenchymal stem cells. In some embodiments, co-administration of the compositions includes administering one composition within 0.5, 1, 2, 4, 6, 8, 10, 12, 16, 20, or 24 hours of a second composition. In some embodiments, the two compositions are administered simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both the LLP2A-Ale conjugates and the mesenchymal stem cells. In other embodiments, the compositions can be formulated separately.

Administration of the compounds of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra joint, parenteral, intra-arteriole, intradermal, intraventricular, intracranial, intraperitoneal, intralesional, intranasal, rectal, vaginal, or by inhalation. In some embodiments, one or both of the LLP2A-bisphosphonate conjugates and the mesenchymal stem cells are administered locally at a site of inflammation (e.g., a joint). In some embodiments, one or both of the LLP2A-bisphosphonate conjugates and the mesenchymal stem cells are administered systemically.

V. Methods of Treating Inflammation

The conjugates as described herein (e.g., LLP2A-Ale) can be used alone or in combination with mesenchymal stem cells for treating inflammation or promoting an anti-inflammatory or immunomodulatory effect, e.g., at a site of inflammation in a subject in need thereof. In some embodiments, a compound provided herein can promote mesenchymal stem cell migration to a site of inflammation that is in proximity to bone, such as the inflammatory synovium, in an individual with an inflammatory disease. In some embodiments, the present invention provides a method of preventing and/or treating bone- or joint-associated inflammatory disease, wherein the method includes administering to a subject in need thereof, a therapeutically effective amount of an LLP2A-bisphosphonate conjugate (e.g., a compound of Formula I), and optionally in combination with mesenchymal stem cells.

In some embodiments, the methods of the present invention promote an anti-inflammatory response by administering an LLP2A-bisphosphonate conjugate (e.g., a compound of Formula I). Administration of a compound as described herein can promote a local anti-inflammatory response and/or systemic anti-inflammatory response. In some embodiments, the administration of the compound, optionally in combination with mesenchymal stem cells, promotes systemic anti-inflammatory response. In other embodiments, local application of the compound, optionally in combination with mesenchymal stem cells, achieves local anti-inflammatory response (e.g., at a site of inflammation).

In some other embodiments, the methods of the present invention promote an immune response by administering an LLP2A-bisphosphonate conjugate (e.g., a compound of Formula I). Administration of a compound as described herein can promote a local immune response and/or systemic immune response. In some embodiments, the administration of the compound, optionally in combination with mesenchymal stem cells, promotes systemic immune response. In other embodiments, local application of the compound, optionally in combination with mesenchymal stem cells, achieves local immune response (e.g., at a site of inflammation).

In some embodiments, the methods of the present invention enhance an anti-inflammatory or immunomodulatory property of mesenchymal stem cells (e.g., endogenous mesenchymal stem cells of a subject or exogenous mesenchymal stem cells administered to a subject) by administering an LLP2A-bisphosphonate conjugate (e.g., a compound of Formula I). In some embodiments, the administration of a compound as described herein, optionally in combination with mesenchymal stem cells, promotes systemic enhancement of a mesenchymal stem cell anti-inflammatory or immunomodulatory property or properties. In other embodiments, local application of the compound, optionally in combination with mesenchymal stem cells, achieves local enhancement of a mesenchymal stem cell anti-inflammatory or immunomodulatory property or properties (e.g., at a site of inflammation).

In some embodiments, the methods of the present invention reduce one or more signs or symptoms of arthritis pain, e.g., in rheumatoid arthritis or inflammatory arthritis, by administering an LLP2A-bisphosphonate conjugate (e.g., a compound of Formula I). In some embodiments, the compound is administered in combination with mesenchymal stem cells. In some embodiments, the signs or symptoms of arthritis pain that are reduced include, but are not limited to, inflammation, swelling, stiffness, or tenderness of one or more joints, e.g., in the hands, wrists, elbows, ankles, toes, knees, or neck, or inflammation of connective tissues adjacent to a nerve resulting in numbness or tingling.

In some embodiments, the methods of the present invention reduce, slow, or inhibit structural deterioration, e.g., cartilage and bone loss, resulting from inflammation in arthritis, e.g., in rheumatoid arthritis or inflammatory arthritis, by administering an LLP2A-bisphosphonate conjugate (e.g., a compound of Formula I). In some embodiments, the compound is administered in combination with mesenchymal stem cells. In some embodiments, the methods of the present invention reduce cartilage or bone loss caused by inflammation in arthritis by at least 10%, 20%, 30%, 40%, 50% or more relative to a control subject (e.g., an untreated subject having arthritis). In some embodiments, the methods of the present invention delay the cartilage or bone loss caused by inflammation in arthritis by months or years relative to a control subject (e.g., an untreated subject having arthritis).

Individuals to be treated using methods of the present invention can be any mammal. Such individuals include a dog, cat, horse, cow, or goat, particularly a commercially important animal or a domesticated animal, more particularly a human. In some embodiments, a subject in need of treatment according to the methods of the present invention is a subject who has been diagnosed with or is suspected of having an inflammatory condition, disease, or disorder.

Inflammatory Conditions, Diseases, and Disorders

In some embodiments, the inflammatory condition, disease, or disorder is a primary inflammatory disease or disorder. In some embodiments, the inflammatory condition, disease, or disorder is a primary inflammatory bone disease. In some embodiments, the primary inflammatory condition, disease, or disorder is selected from arthritis, inflammatory arthritis, rheumatoid arthritis, synovitis, juvenile rheumatoid arthritis, ankylosing spondylitis, psoriatic arthritis, spondylarthritis, and osteoarthritis. In some embodiments, the inflammatory condition, disease, or disorder is rheumatoid arthritis. In some embodiments, the inflammatory condition, disease, or disorder is synovitis.

In some embodiments, the inflammatory condition, disease, or disorder is localized to a bone, joint, or bone-associated tissue. In some embodiments, the inflammatory condition, disease, or disorder is localized to one or more joints, e.g., synovial joints (e.g., knee, hip, elbow, or wrist).

VI. Examples

The following example is offered to illustrate, but not to limit, the claimed invention.

This example illustrates the use of LLP2A-Ale in reducing inflammation and reducing immune system activity and in the treatment of bone loss associated with inflammatory disease.

To analyze the therapeutic effects of LLP2A-Ale on rheumatoid arthritis, including anti-inflammatory effects and bone loss associated with rheumatoid arthritis, an animal model of rheumatoid arthritis was studied. The model "K/B×N" was obtained by crossing KRN TCR transgenic C57BL/6 mice with NOD mice. This serum-transfer-induced arthritis (K/B×N model) is induced by antibodies against glucose 6-phosphate isomerase (GPI), and shares many features with human RA including auto-antibodies production, synovitis, leukocytes invasion, pannus formation, cartilage damage and bone erosion. Moreover, serum-transfer induced arthritis is characterized by enhanced osteoclastogenesis and consecutive local and systemic bone loss.

Figure 1B:
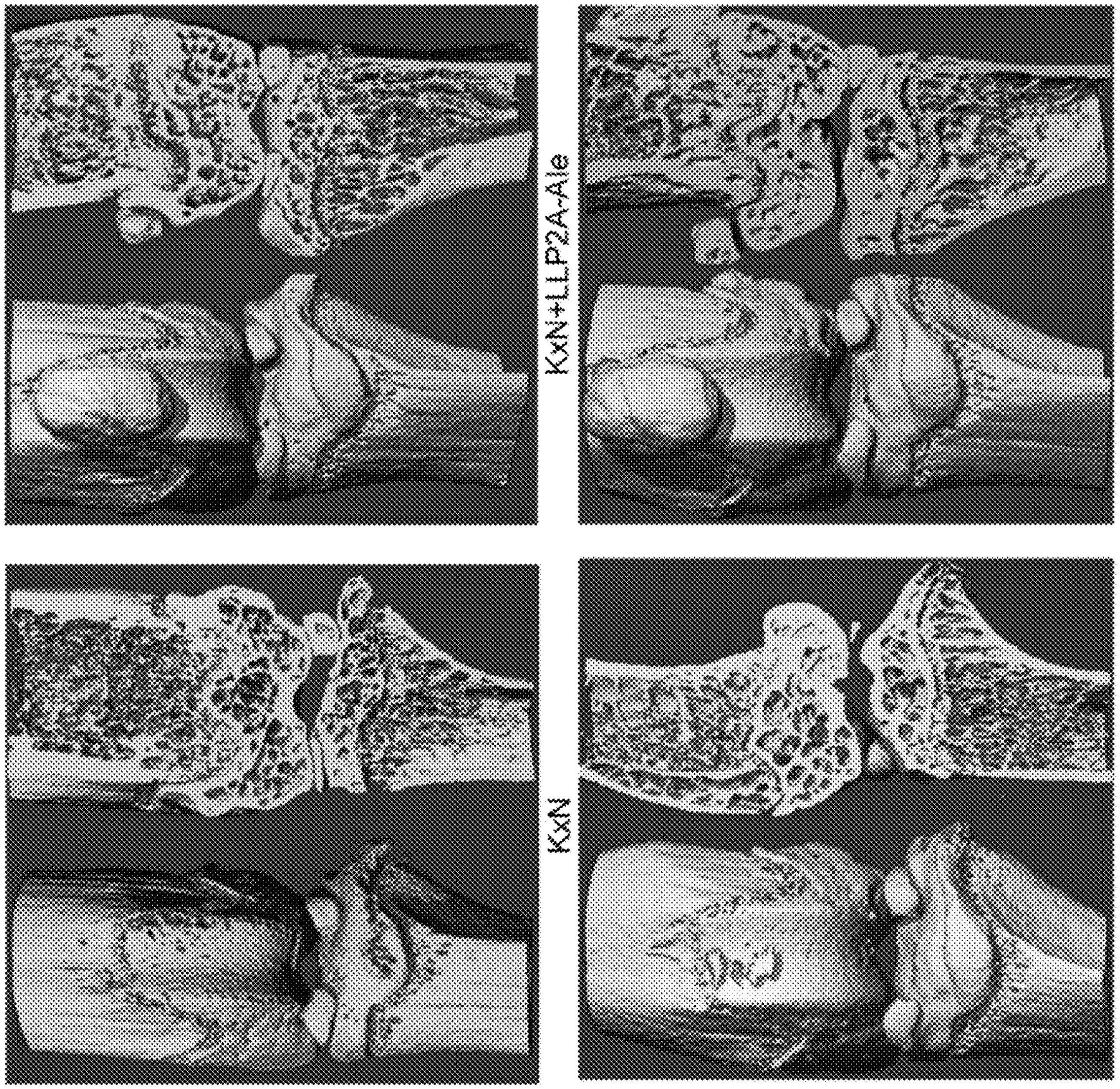

Bone volume was assessed in mice with RA after receiving serum or LLP2A-Ale therapy. C57Bl/6 mice received either K/B×N serum (100 μl/mouse IV at days 0 and 1) and placebo (e.g., vehicle), or K/B×N serum (100 μl/mouse IV at days 0 and 1) and LLP2A-Ale (100 μg/kg by IV administration at day 4). Mice from the two groups were sacrificed at day 25 or day 46 and bone volume/tissue volume fraction were measured by microCT at the distal femur and the proximal tibiae. In mice that had received K/B×N serum (100 μl/mouse IV at days 0 and 1), joint swelling and trabecular bone loss were significant from day 7 and were 22% and 19% lower, respectively, in the distal femurs and the proximal tibiae at day 25. See, FIG. 1A. However, bone loss was not detected in the mice receiving LLP2A-Ale treatment (FIG. 1A-B). These results show that LLP2A-Ale administration prevented bone loss.

Figure 2A:
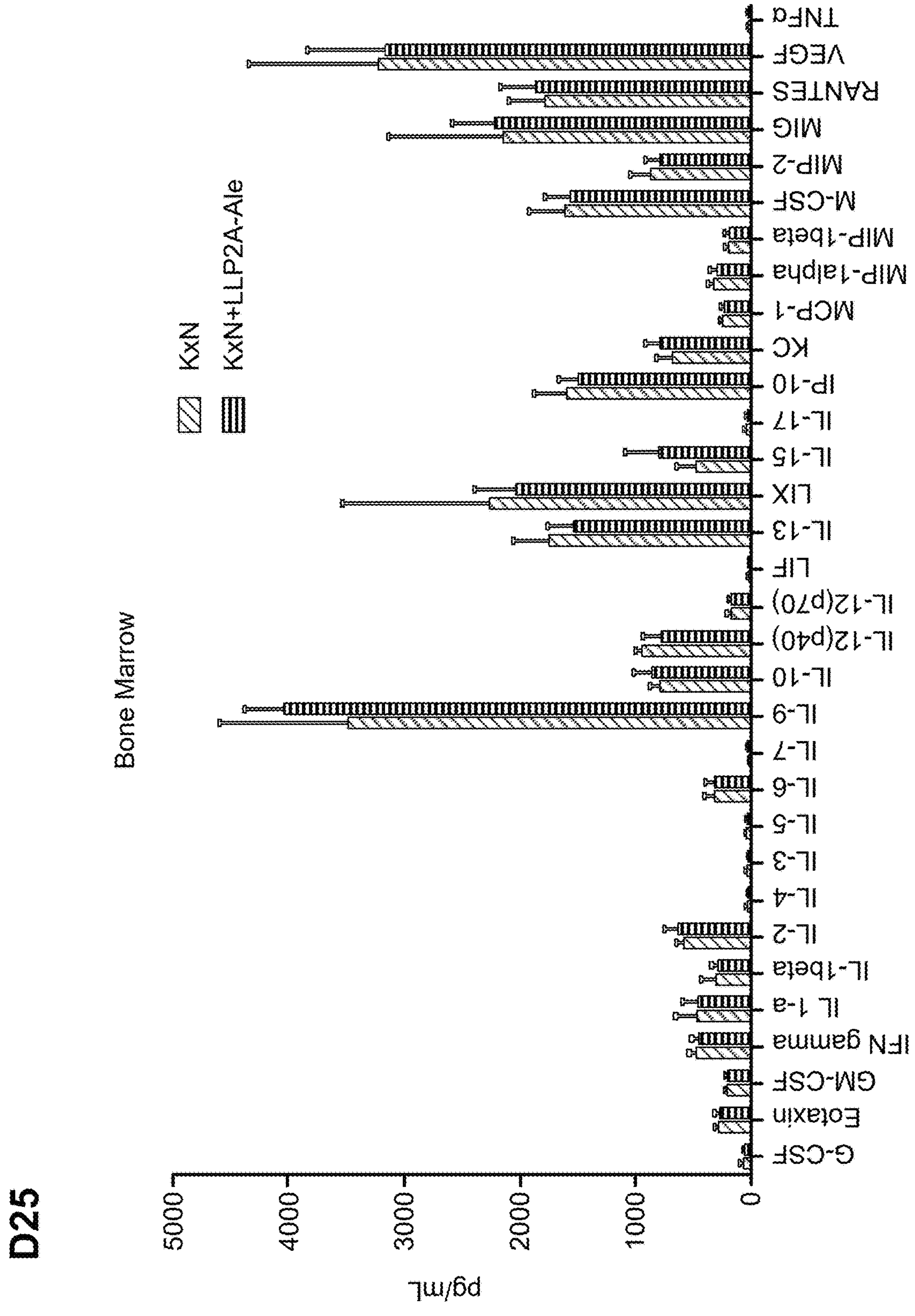
FIG. 2A-B. Cytokine levels at day 25 from bone marrow (A) or serum (B) for rheumatoid arthritis-induced ("K/B×N") mice treated with placebo or LLP2A-Ale.
Figure 2B:
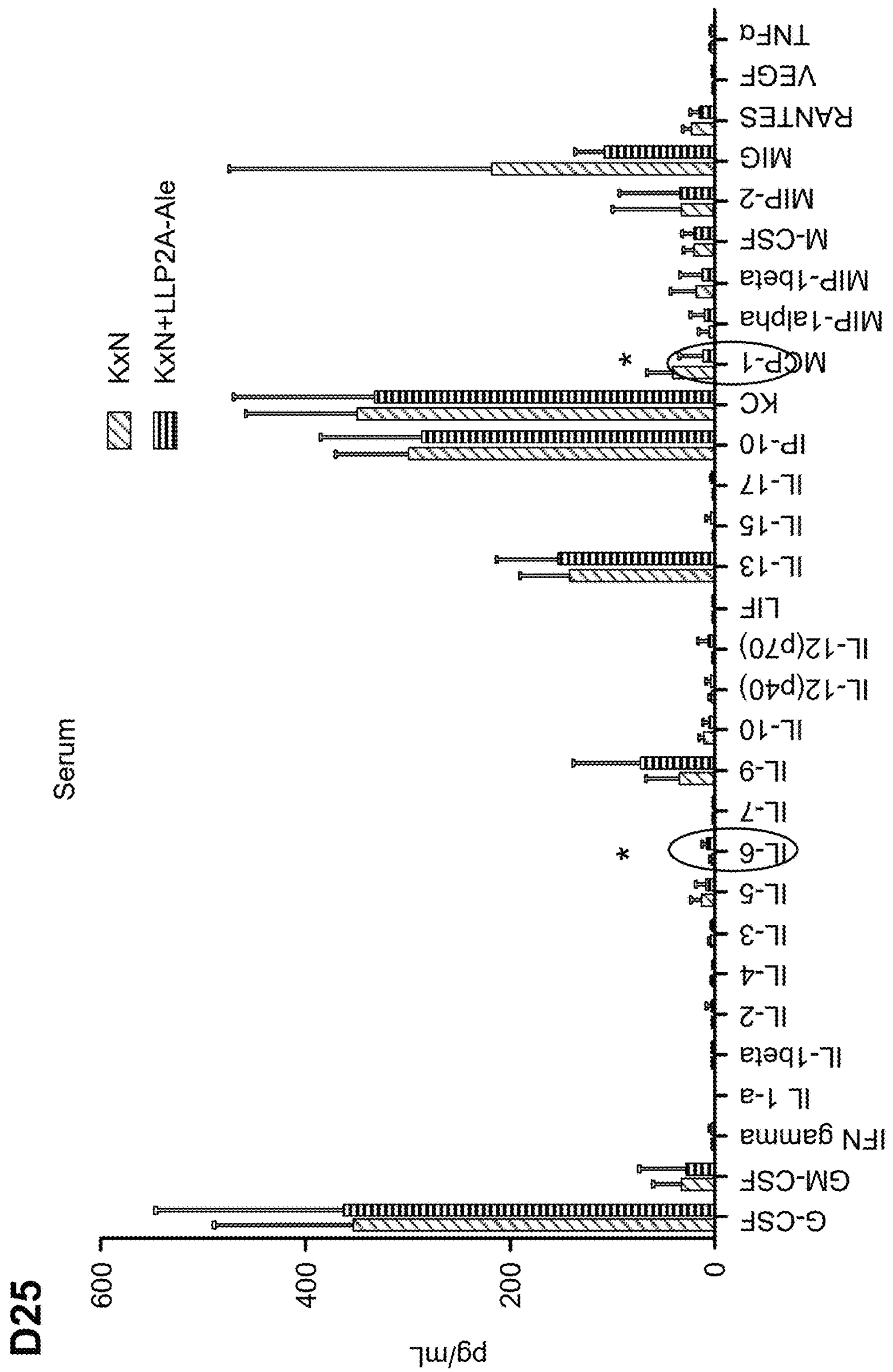
Figure 3A:
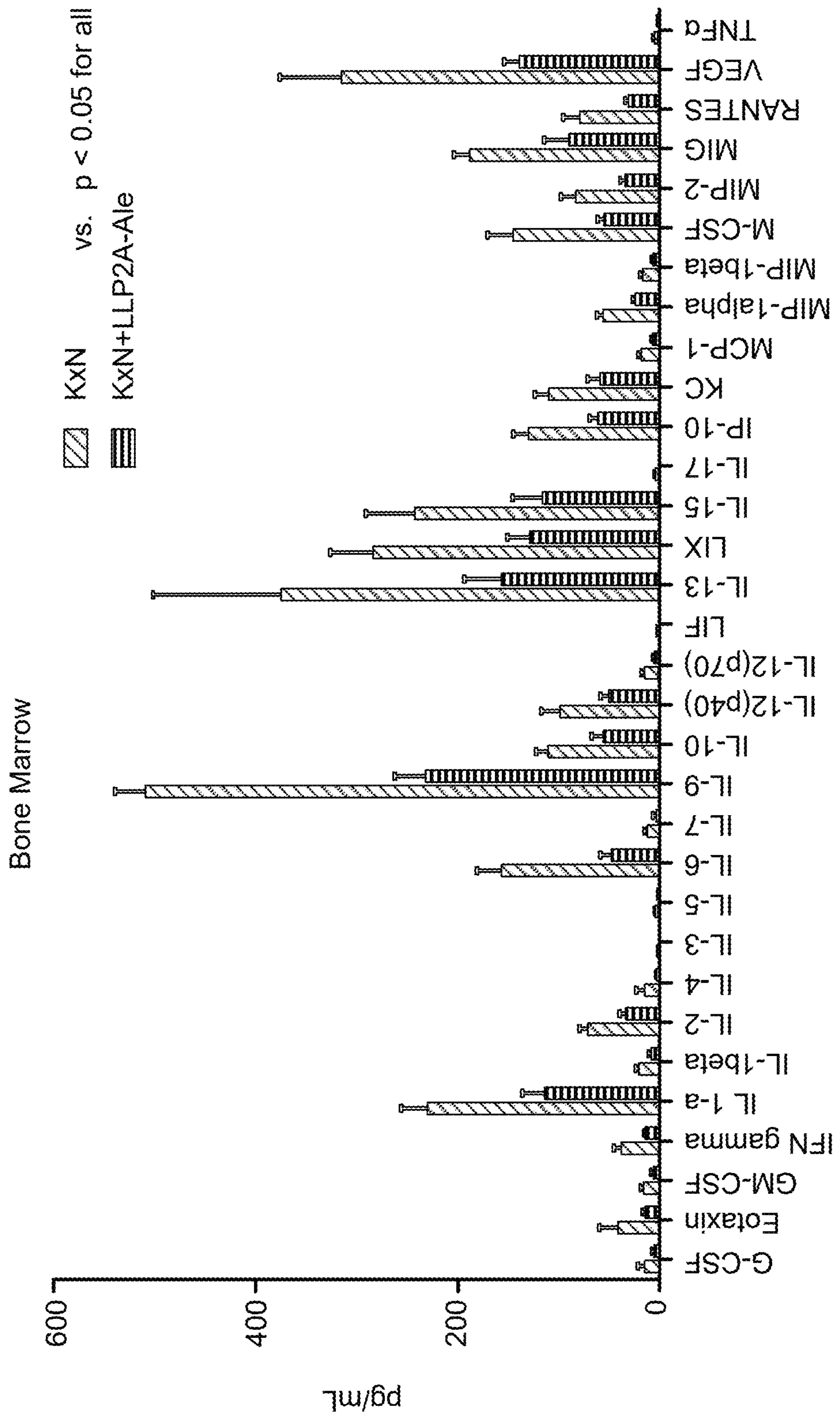
FIG. 3A-B. Cytokine levels at day 46 from bone marrow (A) or serum (B) for rheumatoid arthritis-induced ("K/B×N") mice treated with placebo or LLP2A-Ale. Two monthly LLP2A-Ale injections decreased cytokine activations in the K/B×N serum transfer RA model.
Figure 3B:
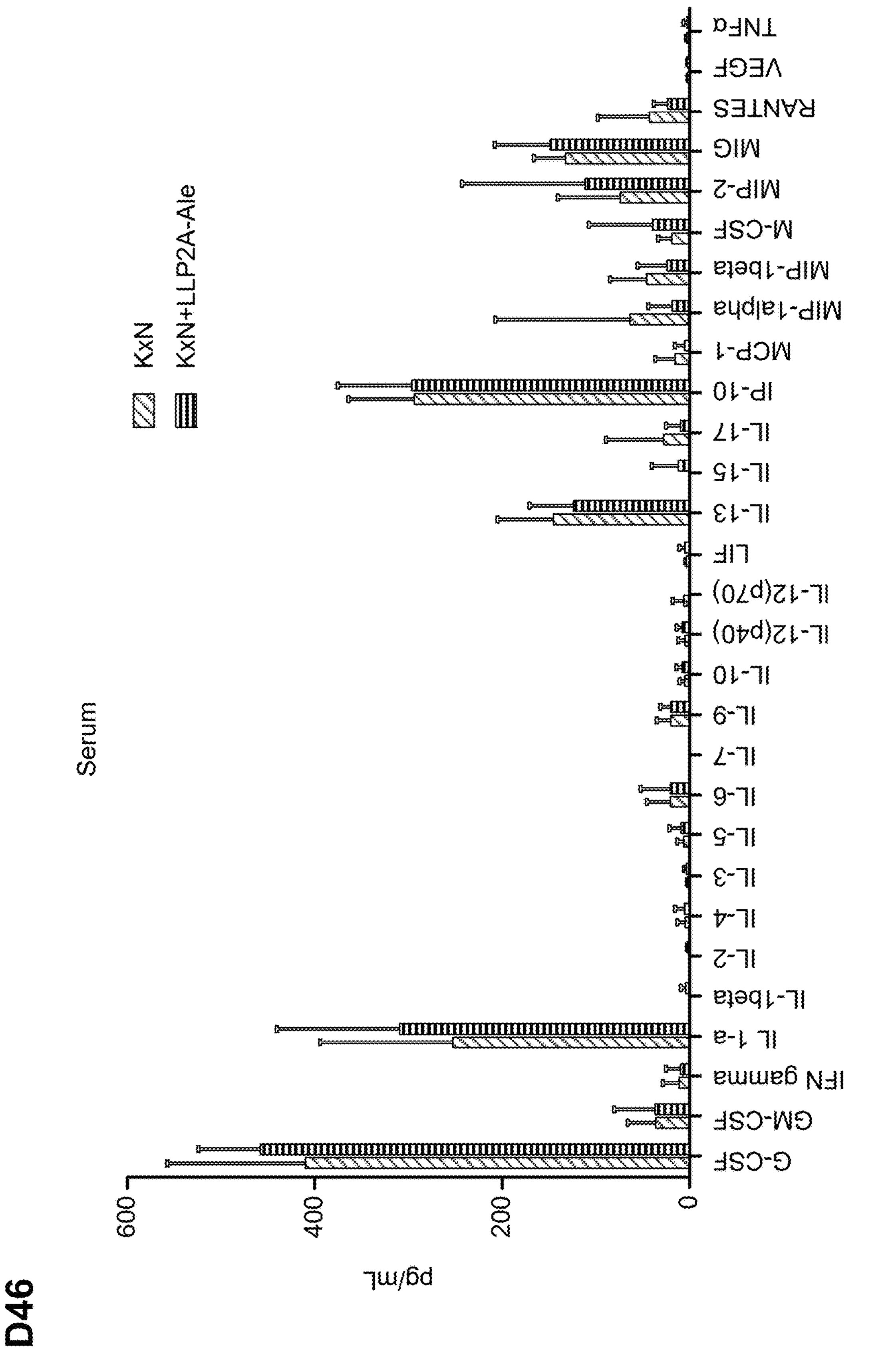

To analyze the effect of LLP2A-Ale on cytokine production, cytokine profiles of bone marrow cells from K/B×N+LLP2A-Ale-treated mice were compared to those from K/B×N+placebo-treated mice. Two-month old C57Bl/6 mice received either K/B×N serum (100 μl/mouse IV at days 0 and 2) and placebo (e.g., vehicle), or K/B×N serum (100 μl/mouse IV at days 0 and 2) and LLP2A-Ale (100 μg/kg by IV administration at day 3). Mice were sacrificed at day 25 or day 36. Mice sacrificed on day 46 were administered a second dose of LLP2A-Ale (100 μg/kg by IV administration) at day 25. Bone marrow cells were extracted from the left femurs and tibiae and serum was taken to measure cytokine (e.g., G-CSF, eotaxin, GM-CSF, IFNγ, IL-1a, IL-1β, IL-2, Il-4, Il-3, IL-5, IL-6, IL-7, IL-9, IL-10, IL-12 (p40), IL-12(p70), LIF, IL-13, LIX, IL-15, IL-17, IP-10 KC, MCP-1, MIP-1α, MIP-1β, M-CSF, MIP-2, MIG, RANTES, VEGF and TNFα) profiles by multiplex (EMD Millipore) at day 25 (FIG. 2A-B) or day 46 (FIG. 3A-B). At day 46, cytokine levels were significantly lower in K/B×N mice treated with LPP2A-Ale compared to the controls (FIG. 3A-B). The lower level of cytokine activation in the LLP2A-Ale treated mice can regulate bone formation and bone resorption, thereby maintaining healthy bone homeostasis.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of reducing or slowing peri-articular bone loss associated with rheumatoid arthritis in a subject, the method comprising administering to the subject a composition comprising a conjugate of an LLP2A peptidomimetic ligand and a bisphosphonate drug.

2. The method of claim 1, wherein the composition comprises a conjugate of LLP2A and Alendronate ("LLP2A-Ale").

3. The method of claim 1, wherein the composition further comprises mesenchymal stem cells.

4. The method of claim 3, wherein one or both of the composition and the mesenchymal stem cells are administered at a subtherapeutic dose.

5. A method of reducing or slowing trabecular bone loss associated with rheumatoid arthritis in a subject, the method comprising administering to the subject a composition comprising a conjugate of an LLP2A peptidomimetic ligand and a bisphosphonate drug.

6. The method of claim 5, wherein the composition comprises a conjugate of LLP2A and Alendronate ("LLP2A-Ale").

7. The method of claim 5, wherein the composition further comprises mesenchymal stem cells.

8. The method of claim 7, wherein one or both of the composition and the mesenchymal stem cells are administered at a subtherapeutic dose.

9. The method of claim 5, wherein the trabecular bone loss is in proximal tibiae.

* * * * *